US011432900B2

(12) United States Patent
Rakic et al.

(10) Patent No.: US 11,432,900 B2
(45) Date of Patent: Sep. 6, 2022

(54) ARTICULATING ARM LIMITER FOR CAVITATIONAL ULTRASOUND THERAPY SYSTEM

(71) Applicant: HISTOSONICS, INC., Ann Arbor, MI (US)

(72) Inventors: Aleksandra Rakic, Ann Arbor, MI (US); Dejan Teofilovic, Ann Arbor, MI (US)

(73) Assignee: HistoSonics, Inc., Plymouth, MN (US)

( * ) Notice: Subject to any disclaimer, the term of this patent is extended or adjusted under 35 U.S.C. 154(b) by 1353 days.

(21) Appl. No.: 14/899,139

(22) PCT Filed: Jul. 3, 2014

(86) PCT No.: PCT/US2014/045455
§ 371 (c)(1),
(2) Date: Dec. 17, 2015

(87) PCT Pub. No.: WO2015/003154
PCT Pub. Date: Jan. 8, 2015

(65) Prior Publication Data
US 2016/0135916 A1  May 19, 2016

Related U.S. Application Data

(60) Provisional application No. 61/842,811, filed on Jul. 3, 2013.

(51) Int. Cl.
A61B 90/50 (2016.01)
A61N 7/02 (2006.01)
(Continued)

(52) U.S. Cl.
CPC ............ A61B 90/50 (2016.02); A61B 8/4218 (2013.01); A61B 8/4405 (2013.01); A61B 90/80 (2016.02);
(Continued)

(58) Field of Classification Search
CPC ........ A61N 7/00; A61N 7/02; A61H 23/0245; A61B 90/50; A61B 8/4218; A61B 8/4405;
(Continued)

(56) References Cited

U.S. PATENT DOCUMENTS 3,243,497 A   3/1966  Kendall et al.
3,679,021 A   7/1972  Goldberg et al.
(Continued)

FOREIGN PATENT DOCUMENTS

CN   1669672 A   9/2005
CN   1732031 A   2/2006
(Continued)

OTHER PUBLICATIONS

Akiyama et al.; Elliptically curved acoustic lens for emitting strongly focused finite-amplitude beams: Application of the spheroidal beam equation model to the theoretical prediction; Acoustical Science and Technology, vol. 26, pp. 279-284, May 2005.
(Continued)

Primary Examiner — Hien N Nguyen
(74) Attorney, Agent, or Firm — Shay Glenn LLP

(57) ABSTRACT

Methods and devices for manipulating an articulating arm of an ultrasound therapy system are provided. In one embodiment an articulating arm comprises a first articulating arm link, a second articulating arm link, a rotating joint configured to rotationally connect the first articulating arm link to the second articulating arm link so that the first and second articulating arm links are substantially perpendicular, and an arm limiter attached to the second articulating arm link, the arm limiter being configured to limit rotation of the second articulating arm link along the rotating joint with respect to the first articulating arm link. An ultrasound therapy transducer and imaging system can be mounted on the articulat-
(Continued)

ing arm. Methods for performing manipulating the arm and system are also provided.

5 Claims, 6 Drawing Sheets

(51) Int. Cl.
*A61B 8/00* (2006.01)
*A61B 90/80* (2016.01)
*A61N 7/00* (2006.01)
*F16C 11/04* (2006.01)
*F16M 13/02* (2006.01)
*A61B 90/00* (2016.01)

(52) U.S. Cl.
CPC .............. *A61N 7/00* (2013.01); *A61N 7/02* (2013.01); *F16C 11/04* (2013.01); *F16M 13/02* (2013.01); *A61B 2090/378* (2016.02); *F16M 2200/04* (2013.01); *F16M 2200/06* (2013.01)

(58) Field of Classification Search
CPC ... A61B 90/80; A61B 2090/378; F16C 11/04; F16M 13/02; F16M 2200/04; F16M 2200/06
See application file for complete search history.

(56) References Cited

U.S. PATENT DOCUMENTS

| | | | |
|---|---|---|---|
| 4,016,749 A | 4/1977 | Wachter | |
| 4,024,501 A | 5/1977 | Herring et al. | |
| 4,051,394 A | 9/1977 | Tieden | |
| 4,117,446 A | 9/1978 | Alais | |
| 4,266,747 A * | 5/1981 | Souder, Jr | F16M 11/14 248/123.11 |
| 4,269,174 A | 5/1981 | Adair | |
| 4,277,367 A | 7/1981 | Madsen et al. | |
| 4,351,038 A | 9/1982 | Alais | |
| 4,406,153 A | 9/1983 | Ophir et al. | |
| 4,440,025 A | 4/1984 | Hayakawa et al. | |
| 4,447,031 A * | 5/1984 | Souder, Jr | F16M 11/126 248/281.11 |
| 4,453,408 A | 6/1984 | Clayman | |
| 4,483,345 A | 11/1984 | Miwa | |
| 4,548,374 A * | 10/1985 | Thompson | B23Q 1/5468 248/123.11 |
| 4,549,533 A | 10/1985 | Cain et al. | |
| 4,550,606 A | 11/1985 | Drost | |
| 4,551,794 A * | 11/1985 | Sandell | F21S 6/001 362/392 |
| 4,575,330 A | 3/1986 | Hull | |
| 4,622,972 A | 11/1986 | Giebeler, Jr. | |
| 4,625,731 A | 12/1986 | Quedens et al. | |
| 4,641,378 A | 2/1987 | McConnell et al. | |
| 4,669,483 A | 6/1987 | Hepp et al. | |
| 4,689,986 A | 9/1987 | Carson et al. | |
| 4,757,820 A | 7/1988 | Itoh | |
| 4,791,915 A | 12/1988 | Barsotti et al. | |
| 4,819,621 A | 4/1989 | Ueberle et al. | |
| 4,829,491 A | 5/1989 | Saugeon et al. | |
| 4,856,107 A | 8/1989 | Dory | |
| 4,865,042 A | 9/1989 | Umemura et al. | |
| 4,888,746 A | 12/1989 | Wurster et al. | |
| 4,890,267 A | 12/1989 | Rudolph | |
| 4,922,917 A | 5/1990 | Dory | |
| 4,938,217 A | 7/1990 | Lele | |
| 4,957,099 A | 9/1990 | Hassler | |
| 4,973,980 A | 11/1990 | Howkins et al. | |
| 4,975,856 A | 12/1990 | Vold et al. | |
| 4,984,575 A | 1/1991 | Uchiyama et al. | |
| 4,991,151 A | 2/1991 | Dory | |
| 4,995,012 A | 2/1991 | Dory | |
| RE33,590 E | 5/1991 | Dory | |
| 5,014,686 A | 5/1991 | Schafer | |
| 5,065,751 A | 11/1991 | Wolf | |
| 5,080,101 A | 1/1992 | Dory | |
| 5,080,102 A | 1/1992 | Dory | |
| 5,091,893 A | 2/1992 | Smith et al. | |
| 5,092,336 A | 3/1992 | Fink | |
| 5,097,709 A | 3/1992 | Masuzawa et al. | |
| 5,111,822 A | 5/1992 | Dory | |
| 5,143,073 A | 9/1992 | Dory | |
| 5,143,074 A | 9/1992 | Dory | |
| 5,150,711 A | 9/1992 | Dory | |
| 5,158,070 A | 10/1992 | Dory | |
| 5,158,071 A | 10/1992 | Umemura et al. | |
| 5,163,421 A | 11/1992 | Bernstein et al. | |
| 5,165,412 A | 11/1992 | Okazaki | |
| 5,174,294 A | 12/1992 | Saito et al. | |
| 5,209,221 A | 5/1993 | Riedlinger | |
| 5,215,680 A | 6/1993 | D'Arrigo | |
| 5,219,401 A | 6/1993 | Cathignol et al. | |
| 5,222,806 A * | 6/1993 | Roberts, III | F21S 6/003 248/122.1 |
| 5,230,340 A | 7/1993 | Rhyne | |
| 5,295,484 A | 3/1994 | Marcus et al. | |
| 5,316,000 A | 5/1994 | Chapelon et al. | |
| 5,336,982 A | 8/1994 | Backes | |
| 5,354,258 A | 10/1994 | Dory | |
| 5,380,411 A | 1/1995 | Schlief | |
| 5,393,296 A | 2/1995 | Rattner | |
| 5,409,002 A | 4/1995 | Pell | |
| 5,431,621 A | 7/1995 | Dory | |
| 5,435,311 A | 7/1995 | Umemura et al. | |
| 5,443,069 A | 8/1995 | Schaetzle | |
| 5,450,305 A | 9/1995 | Boys et al. | |
| 5,469,852 A | 11/1995 | Nakamura et al. | |
| 5,474,071 A | 12/1995 | Chapelon et al. | |
| 5,474,531 A | 12/1995 | Carter | |
| 5,490,051 A * | 2/1996 | Messana | F21V 7/18 362/401 |
| 5,501,655 A | 3/1996 | Rolt et al. | |
| 5,520,188 A | 5/1996 | Hennige et al. | |
| 5,523,058 A | 6/1996 | Umemura et al. | |
| 5,524,620 A | 6/1996 | Rosenschein | |
| 5,540,909 A | 7/1996 | Schutt | |
| 5,542,935 A | 8/1996 | Unger et al. | |
| 5,558,092 A | 9/1996 | Unger et al. | |
| 5,563,346 A | 10/1996 | Bartelt et al. | |
| 5,566,675 A | 10/1996 | Li et al. | |
| 5,573,497 A | 11/1996 | Chapelon | |
| 5,580,575 A | 12/1996 | Unger et al. | |
| 5,582,578 A | 12/1996 | Zhong et al. | |
| 5,590,657 A | 1/1997 | Cain et al. | |
| 5,601,526 A | 2/1997 | Chapelon et al. | |
| 5,617,862 A | 4/1997 | Cole et al. | |
| 5,648,098 A | 7/1997 | Porter | |
| 5,666,954 A | 9/1997 | Chapelon et al. | |
| 5,676,452 A | 10/1997 | Scholz | |
| 5,676,692 A | 10/1997 | Sanghvi et al. | |
| 5,678,554 A | 10/1997 | Hossack et al. | |
| 5,694,936 A | 12/1997 | Fujimoto et al. | |
| 5,695,460 A | 12/1997 | Siege et al. | |
| 5,717,657 A | 2/1998 | Ruffa | |
| 5,724,972 A | 3/1998 | Petrofsky | |
| 5,743,863 A | 4/1998 | Chapelon | |
| 5,753,929 A | 5/1998 | Bliss | |
| 5,759,162 A | 6/1998 | Oppelt et al. | |
| 5,766,138 A | 6/1998 | Rattner | |
| 5,769,790 A | 6/1998 | Watkins et al. | |
| 5,797,848 A | 8/1998 | Marian et al. | |
| 5,823,962 A | 10/1998 | Schaetzle et al. | |
| 5,827,204 A | 10/1998 | Grandia et al. | |
| 5,836,896 A | 11/1998 | Rosenschein | |
| 5,849,727 A | 12/1998 | Porter et al. | |
| 5,873,902 A | 2/1999 | Sanghvi et al. | |
| 5,879,314 A | 3/1999 | Peterson et al. | |
| 5,932,807 A | 8/1999 | Mallart | |
| 5,947,904 A | 9/1999 | Hossack et al. | |
| 6,001,069 A | 12/1999 | Tachibana et al. | |
| 6,022,309 A | 2/2000 | Celliers et al. | |

(56) References Cited

U.S. PATENT DOCUMENTS

| | | |
|---|---|---|
| 6,036,667 A | 3/2000 | Manna et al. |
| 6,088,613 A | 7/2000 | Unger |
| 6,093,883 A | 7/2000 | Sanghvi et al. |
| 6,113,558 A | 9/2000 | Rosenschein et al. |
| 6,126,607 A | 10/2000 | Whitmore, III et al. |
| 6,128,958 A | 10/2000 | Cain |
| 6,143,018 A | 11/2000 | Beuthan et al. |
| 6,165,144 A | 12/2000 | Talish et al. |
| 6,176,842 B1 | 1/2001 | Tachibana et al. |
| 6,296,619 B1 | 10/2001 | Brisken et al. |
| 6,308,585 B1 | 10/2001 | Nilsson et al. |
| 6,308,710 B1 | 10/2001 | Silva |
| 6,309,355 B1 | 10/2001 | Cain et al. |
| 6,313,595 B2 | 11/2001 | Swanson et al. |
| 6,318,146 B1 | 11/2001 | Madsen et al. |
| 6,321,109 B2 | 11/2001 | Ben-Haim et al. |
| 6,338,566 B1 | 1/2002 | Verdier |
| 6,344,489 B1 | 2/2002 | Spears |
| 6,391,020 B1 | 5/2002 | Kurtz et al. |
| 6,413,216 B1 | 7/2002 | Cain et al. |
| 6,419,648 B1 | 7/2002 | Vitek et al. |
| 6,470,204 B1 | 10/2002 | Uzgiris et al. |
| 6,488,639 B1 | 12/2002 | Ribault et al. |
| 6,490,469 B2 | 12/2002 | Candy |
| 6,500,141 B1 | 12/2002 | Irion et al. |
| 6,506,154 B1 | 1/2003 | Ezion et al. |
| 6,506,171 B1 | 1/2003 | Vitek et al. |
| 6,508,774 B1 | 1/2003 | Acker et al. |
| 6,511,428 B1 | 1/2003 | Azuma et al. |
| 6,511,444 B2 | 1/2003 | Hynynen et al. |
| 6,522,142 B1 | 2/2003 | Freundlich |
| 6,524,251 B2 | 2/2003 | Rabiner et al. |
| 6,536,553 B1 | 3/2003 | Scanlon |
| 6,543,272 B1 | 4/2003 | Vitek |
| 6,556,750 B2 | 4/2003 | Constantino et al. |
| 6,559,644 B2 | 5/2003 | Froundlich et al. |
| 6,576,220 B2 | 6/2003 | Unger |
| 6,599,288 B2 | 7/2003 | Maguire et al. |
| 6,607,498 B2 | 8/2003 | Eshel |
| 6,612,988 B2 | 9/2003 | Maor et al. |
| 6,613,004 B1 | 9/2003 | Vitek et al. |
| 6,613,005 B1 | 9/2003 | Friedman et al. |
| 6,626,854 B2 | 9/2003 | Friedman et al. |
| 6,626,855 B1 | 9/2003 | Weng et al. |
| 6,645,162 B2 | 11/2003 | Friedman et al. |
| 6,648,839 B2 | 11/2003 | Manna et al. |
| 6,666,833 B1 | 12/2003 | Friedman et al. |
| 6,685,640 B1 | 2/2004 | Fry et al. |
| 6,685,657 B2 | 2/2004 | Jones |
| 6,705,994 B2 | 3/2004 | Vortman et al. |
| 6,719,449 B1 | 4/2004 | Laugharn, Jr. et al. |
| 6,719,694 B2 | 4/2004 | Weng et al. |
| 6,735,461 B2 | 5/2004 | Vitek et al. |
| 6,736,814 B2 | 5/2004 | Manna et al. |
| 6,750,463 B1 | 6/2004 | Riley |
| 6,770,031 B2 | 8/2004 | Hynynen et al. |
| 6,775,438 B1 | 8/2004 | Gaedke et al. |
| 6,788,977 B2 | 9/2004 | Fenn et al. |
| 6,790,180 B2 | 9/2004 | Vitek |
| 6,820,160 B1 | 11/2004 | Allman |
| 6,852,082 B2 | 2/2005 | Strickberger et al. |
| 6,869,439 B2 | 3/2005 | White et al. |
| 6,890,332 B2 | 5/2005 | Truckai et al. |
| 6,929,609 B2 | 8/2005 | Asafusa |
| 7,004,282 B2 | 2/2006 | Manna et al. |
| 7,059,168 B2 | 6/2006 | Hibi et al. |
| 7,128,711 B2 | 10/2006 | Medan et al. |
| 7,128,719 B2 | 10/2006 | Rosenberg |
| 7,175,596 B2 | 2/2007 | Vitek et al. |
| 7,196,313 B2 | 3/2007 | Quinones |
| 7,223,239 B2 | 5/2007 | Schulze et al. |
| 7,258,674 B2 | 8/2007 | Cribbs et al. |
| 7,273,458 B2 | 9/2007 | Prausnitz et al. |
| 7,273,459 B2 | 9/2007 | Desilets et al. |
| 7,300,414 B1 | 11/2007 | Holland et al. |
| 7,311,679 B2 | 12/2007 | Desilets et al. |
| 7,331,951 B2 | 2/2008 | Eshel et al. |
| 7,341,569 B2 | 3/2008 | Soltani et al. |
| 7,347,855 B2 | 3/2008 | Eshel et al. |
| 7,358,226 B2 | 4/2008 | Dayton et al. |
| 7,359,640 B2 | 4/2008 | Onde et al. |
| 7,367,948 B2 | 5/2008 | O'Donnell et al. |
| 7,374,551 B2 | 5/2008 | Liang et al. |
| 7,377,900 B2 | 5/2008 | Vitek et al. |
| 7,429,249 B1 | 9/2008 | Winder et al. |
| 7,431,704 B2 | 10/2008 | Babaev |
| 7,442,168 B2 | 10/2008 | Novak |
| 7,462,488 B2 | 12/2008 | Madsen et al. |
| 7,559,905 B2 | 7/2009 | Kagosaki et al. |
| 7,656,638 B2 | 2/2010 | Laakso et al. |
| 7,695,437 B2 | 4/2010 | Quistgaard et al. |
| 7,714,481 B2 | 5/2010 | Sakai |
| 7,771,359 B2 | 8/2010 | Adam |
| 7,967,763 B2 | 6/2011 | Deem et al. |
| 8,057,408 B2 | 11/2011 | Cain et al. |
| 8,295,912 B2 | 10/2012 | Gertner |
| 8,333,115 B1 | 12/2012 | Garvey et al. |
| 8,337,407 B2 | 12/2012 | Quistgaard et al. |
| 8,342,467 B2 * | 1/2013 | Stachowski .............. A61B 8/00 248/280.11 |
| 8,376,970 B2 | 2/2013 | Babaev |
| 8,539,813 B2 | 9/2013 | Cain et al. |
| 8,568,339 B2 | 10/2013 | Rybyanets |
| 8,636,664 B2 | 1/2014 | Brannan |
| 8,715,187 B2 | 5/2014 | Landberg Davis et al. |
| 8,845,537 B2 | 9/2014 | Tanaka et al. |
| 8,932,239 B2 | 1/2015 | Sokka et al. |
| 9,028,434 B2 | 5/2015 | Tanaka |
| 9,049,783 B2 | 6/2015 | Teofilovic |
| 9,061,131 B2 | 6/2015 | Jahnke et al. |
| 9,144,694 B2 | 9/2015 | Cain |
| 9,220,476 B2 | 12/2015 | Coussios et al. |
| 9,228,730 B1 * | 1/2016 | Inbody .................... F21V 21/30 |
| 9,302,124 B2 | 4/2016 | Konofagou et al. |
| 9,457,201 B2 | 10/2016 | Hoelscher et al. |
| 9,763,688 B2 | 9/2017 | Stulen et al. |
| 10,046,181 B2 | 8/2018 | Barthe et al. |
| 10,058,352 B2 | 8/2018 | Carveil et al. |
| 10,130,828 B2 | 11/2018 | Vortman et al. |
| 10,751,125 B2 | 8/2020 | Levy et al. |
| 10,791,991 B2 | 10/2020 | Burkett et al. |
| 10,799,209 B2 | 10/2020 | Lahti et al. |
| 10,820,813 B2 | 11/2020 | Alpert |
| 10,847,264 B2 | 11/2020 | Mansker et al. |
| 10,869,603 B2 | 12/2020 | Millett et al. |
| 10,869,633 B2 | 12/2020 | Burkett |
| 10,869,648 B2 | 12/2020 | Hubbard et al. |
| 10,874,353 B2 | 12/2020 | Assif |
| 10,874,409 B2 | 12/2020 | Matsubara et al. |
| 11,272,845 B2 | 3/2022 | Cheline et al. |
| 11,298,030 B2 | 4/2022 | Davies et al. |
| 11,311,271 B2 | 4/2022 | Stigall et al. |
| 11,324,410 B2 | 5/2022 | Burkett |
| 2001/0039420 A1 | 11/2001 | Burbank et al. |
| 2001/0041163 A1 | 11/2001 | Sugita et al. |
| 2002/0045890 A1 | 4/2002 | Celliers et al. |
| 2002/0078964 A1 | 6/2002 | Kovac et al. |
| 2002/0099356 A1 | 7/2002 | Unger et al. |
| 2002/0145091 A1 | 10/2002 | Talish et al. |
| 2003/0092982 A1 | 5/2003 | Eppstein |
| 2003/0112922 A1 | 6/2003 | Burdette et al. |
| 2003/0149352 A1 | 8/2003 | Liang et al. |
| 2003/0157025 A1 | 8/2003 | Unger et al. |
| 2003/0169591 A1 * | 9/2003 | Cochran ................ F21L 4/005 362/158 |
| 2003/0181833 A1 | 9/2003 | Faragalla et al. |
| 2003/0199857 A1 | 10/2003 | Eizenhofer |
| 2003/0221561 A1 | 12/2003 | Milo |
| 2003/0236539 A1 | 12/2003 | Rabiner et al. |
| 2004/0127815 A1 | 7/2004 | Marchitto et al. |
| 2004/0138563 A1 | 7/2004 | Moehring et al. |
| 2004/0236248 A1 | 11/2004 | Svedman |
| 2004/0243021 A1 | 12/2004 | Murphy et al. |
| 2004/0260214 A1 | 12/2004 | Echt et al. |

(56) References Cited

U.S. PATENT DOCUMENTS

| | | |
|---|---|---|
| 2005/0020945 A1 | 1/2005 | Tosaya et al. |
| 2005/0038339 A1 | 2/2005 | Chauhan et al. |
| 2005/0038361 A1 | 2/2005 | Zhong et al. |
| 2005/0152561 A1 | 7/2005 | Spencer |
| 2005/0154314 A1 | 7/2005 | Quistgaard |
| 2005/0234438 A1 | 10/2005 | Mast et al. |
| 2005/0283098 A1 | 12/2005 | Conston et al. |
| 2006/0060991 A1 | 3/2006 | Holsteyns et al. |
| 2006/0074303 A1 | 4/2006 | Chornenky et al. |
| 2006/0173387 A1 | 8/2006 | Hansmann et al. |
| 2006/0206028 A1 | 9/2006 | Lee et al. |
| 2006/0241466 A1 | 10/2006 | Ottoboni et al. |
| 2006/0241523 A1 | 10/2006 | Sinelnikov et al. |
| 2006/0241533 A1 | 10/2006 | Geller |
| 2006/0264760 A1 | 11/2006 | Liu et al. |
| 2006/0293630 A1 | 12/2006 | Manna et al. |
| 2007/0010805 A1 | 1/2007 | Fedewa et al. |
| 2007/0016039 A1 | 1/2007 | Vortman et al. |
| 2007/0044562 A1 | 3/2007 | Sarr |
| 2007/0065420 A1 | 3/2007 | Johnson |
| 2007/0083120 A1 | 4/2007 | Cain et al. |
| 2007/0161902 A1 | 7/2007 | Dan |
| 2007/0167764 A1 | 7/2007 | Hynynen |
| 2007/0205785 A1 | 9/2007 | Nilsson |
| 2007/0219448 A1 | 9/2007 | Seip et al. |
| 2008/0013593 A1 | 1/2008 | Kawabata |
| 2008/0033297 A1 | 2/2008 | Sliwa |
| 2008/0055003 A1 | 3/2008 | Unnikrishnan et al. |
| 2008/0082026 A1 | 4/2008 | Schmidt et al. |
| 2008/0091125 A1 | 4/2008 | Owen et al. |
| 2008/0126665 A1 | 5/2008 | Burr et al. |
| 2008/0177180 A1 | 7/2008 | Azhari et al. |
| 2008/0194965 A1 | 8/2008 | Sliwa et al. |
| 2008/0214964 A1 | 9/2008 | Chapelon et al. |
| 2008/0262345 A1 | 10/2008 | Fichtinger et al. |
| 2008/0262486 A1 | 10/2008 | Zvuloni et al. |
| 2008/0312561 A1 | 12/2008 | Chauhan |
| 2008/0319376 A1 | 12/2008 | Wilcox et al. |
| 2009/0030339 A1 | 1/2009 | Cheng et al. |
| 2009/0112098 A1 | 4/2009 | Vaezy et al. |
| 2009/0177085 A1 | 7/2009 | Maxwell et al. |
| 2009/0198094 A1 | 8/2009 | Fenster et al. |
| 2009/0211587 A1 | 8/2009 | Lawrentschuk |
| 2009/0227874 A1 | 9/2009 | Suri et al. |
| 2009/0230822 A1 | 9/2009 | Kushculey et al. |
| 2009/0287083 A1 | 11/2009 | Kushculey et al. |
| 2010/0011845 A1 | 1/2010 | Laugharn et al. |
| 2010/0056924 A1 | 3/2010 | Powers |
| 2010/0059264 A1 | 3/2010 | Hasegawa et al. |
| 2010/0069797 A1 | 3/2010 | Cain et al. |
| 2010/0125225 A1* | 5/2010 | Gelbart ............... A61N 7/02 601/3 |
| 2010/0152624 A1 | 6/2010 | Tanis et al. |
| 2010/0163694 A1* | 7/2010 | Fadler ............... A61B 8/4218 248/125.2 |
| 2010/0261994 A1 | 10/2010 | Davalos et al. |
| 2010/0274136 A1 | 10/2010 | Cerofolini |
| 2010/0286519 A1 | 11/2010 | Lee et al. |
| 2010/0298744 A1 | 11/2010 | Altshuler et al. |
| 2010/0305432 A1 | 12/2010 | Duhay et al. |
| 2010/0317971 A1 | 12/2010 | Fan et al. |
| 2010/0318002 A1 | 12/2010 | Prus et al. |
| 2011/0054315 A1 | 3/2011 | Roberts et al. |
| 2011/0054363 A1 | 3/2011 | Cain et al. |
| 2011/0112400 A1 | 5/2011 | Emery et al. |
| 2011/0118602 A1 | 5/2011 | Weng et al. |
| 2011/0144490 A1 | 6/2011 | Davis et al. |
| 2011/0144545 A1 | 6/2011 | Fan et al. |
| 2011/0172529 A1 | 7/2011 | Gertner |
| 2011/0178444 A1 | 7/2011 | Slayton et al. |
| 2011/0251528 A1 | 10/2011 | Canney et al. |
| 2011/0257524 A1 | 10/2011 | Gertner |
| 2011/0263967 A1 | 10/2011 | Bailey et al. |
| 2011/0270136 A1 | 11/2011 | Vitek et al. |
| 2011/0319927 A1 | 12/2011 | Nita |
| 2012/0010541 A1 | 1/2012 | Cain et al. |
| 2012/0029353 A1 | 2/2012 | Slayton et al. |
| 2012/0029393 A1 | 2/2012 | Lee |
| 2012/0059264 A1 | 3/2012 | Hope Simpson et al. |
| 2012/0059285 A1 | 3/2012 | Soltani et al. |
| 2012/0092724 A1 | 4/2012 | Pettis |
| 2012/0130288 A1 | 5/2012 | Holland et al. |
| 2012/0136279 A1 | 5/2012 | Tanaka et al. |
| 2012/0158013 A1* | 6/2012 | Stefanchik ............... A61B 34/35 606/130 |
| 2012/0172720 A1 | 7/2012 | Kawabata |
| 2012/0189998 A1 | 7/2012 | Kruecker et al. |
| 2012/0215157 A1 | 8/2012 | Berryman et al. |
| 2012/0232388 A1* | 9/2012 | Curra ............... A61B 8/466 600/438 |
| 2012/0259250 A1 | 10/2012 | Sapozhnikov et al. |
| 2012/0271167 A1 | 10/2012 | Holland et al. |
| 2012/0271223 A1 | 10/2012 | Khanna |
| 2013/0051178 A1 | 2/2013 | Rybyanets |
| 2013/0053691 A1 | 2/2013 | Kawabata et al. |
| 2013/0090579 A1 | 4/2013 | Cain et al. |
| 2013/0102932 A1 | 4/2013 | Cain et al. |
| 2013/0144165 A1 | 6/2013 | Ebbini et al. |
| 2013/0190623 A1 | 7/2013 | Bertolina et al. |
| 2013/0255426 A1 | 10/2013 | Kassow et al. |
| 2013/0289593 A1 | 10/2013 | Hall et al. |
| 2013/0303906 A1 | 11/2013 | Cain et al. |
| 2014/0058293 A1 | 2/2014 | Hynynen et al. |
| 2014/0073995 A1 | 3/2014 | Teofilovic et al. |
| 2014/0100459 A1 | 4/2014 | Xu et al. |
| 2014/0128734 A1 | 5/2014 | Genstler et al. |
| 2014/0200489 A1 | 7/2014 | Behar et al. |
| 2014/0330124 A1 | 11/2014 | Carol |
| 2014/0378832 A1 | 12/2014 | Sanghvi et al. |
| 2015/0011916 A1 | 1/2015 | Cannata et al. |
| 2015/0151141 A1 | 6/2015 | Amal et al. |
| 2015/0190121 A1 | 7/2015 | Slayton et al. |
| 2015/0258352 A1 | 9/2015 | Lin et al. |
| 2015/0290477 A1 | 10/2015 | Jahnke et al. |
| 2015/0297177 A1 | 10/2015 | Boctor et al. |
| 2015/0375015 A1 | 12/2015 | Cain |
| 2016/0151618 A1 | 6/2016 | Powers et al. |
| 2016/0184614 A1 | 6/2016 | Matula et al. |
| 2016/0206867 A1 | 7/2016 | Hossack et al. |
| 2016/0287909 A1 | 10/2016 | Maxwell et al. |
| 2016/0339273 A1 | 11/2016 | Al Mayiah |
| 2017/0000376 A1 | 1/2017 | Partanen et al. |
| 2017/0049463 A1 | 2/2017 | Popovic et al. |
| 2017/0071515 A1 | 3/2017 | Chevillet et al. |
| 2017/0072227 A1 | 3/2017 | Khokhlova et al. |
| 2017/0072228 A1 | 3/2017 | Wang et al. |
| 2017/0120080 A1 | 5/2017 | Phillips et al. |
| 2018/0154186 A1 | 6/2018 | Xu et al. |
| 2019/0216478 A1 | 7/2019 | Maxwell et al. |
| 2019/0275353 A1 | 9/2019 | Cannata et al. |
| 2020/0164231 A1 | 5/2020 | Cannata et al. |
| 2020/0253550 A1 | 8/2020 | Nair |
| 2020/0260964 A1 | 8/2020 | Collins et al. |
| 2020/0330039 A1 | 10/2020 | Burkett et al. |
| 2020/0330075 A1 | 10/2020 | O'Reilly et al. |
| 2022/0079563 A1 | 3/2022 | Kemp |

FOREIGN PATENT DOCUMENTS

| | | |
|---|---|---|
| CN | 201197744 Y | 2/2009 |
| CN | 102292123 A | 12/2011 |
| CN | 102481164 A | 5/2012 |
| CN | 102665585 A | 9/2012 |
| CN | 103537016 A | 1/2014 |
| CN | 103648361 A | 3/2014 |
| CN | 103812477 A | 5/2014 |
| CN | 104013444 A | 9/2014 |
| CN | 104135938 A | 11/2014 |
| DE | 3220751 A1 | 12/1983 |
| DE | 3544628 A1 | 6/1987 |
| DE | 3817094 A1 | 11/1989 |
| DE | 4012760 A1 | 5/1992 |
| EP | 0017382 | 10/1980 |
| EP | 0320303 A2 | 6/1989 |

(56) References Cited

FOREIGN PATENT DOCUMENTS

| | | |
|---|---|---|
| EP | 0332871 A2 | 9/1989 |
| EP | 0384831 A2 | 8/1990 |
| EP | 0755653 A1 | 1/1997 |
| EP | 1374785 A1 | 1/2004 |
| EP | 1504713 A1 | 2/2005 |
| EP | 2397188 A1 | 12/2011 |
| EP | 2759003 B1 | 8/2020 |
| EP | 3545829 B1 | 3/2022 |
| EP | 3060129 B1 | 4/2022 |
| EP | 2914166 B1 | 5/2022 |
| GB | 2099582 A | 12/1982 |
| JP | 60-80779 A | 5/1985 |
| JP | 61-196718 A | 8/1986 |
| JP | HEI 2-215451 | 8/1990 |
| JP | H0422351 A | 1/1992 |
| JP | HEI 6-197907 A | 7/1994 |
| JP | HEI 7-504339 A | 5/1995 |
| JP | 08-84740 A | 4/1996 |
| JP | 06-304178 A | 5/1996 |
| JP | 08-131454 A | 5/1996 |
| JP | 09-55571 A | 2/1997 |
| JP | HEI 10-512477 | 12/1998 |
| JP | 2000300559 A | 10/2000 |
| JP | 2003-510159 A | 3/2003 |
| JP | 2004-505660 A | 2/2004 |
| JP | 2004249106 A | 9/2004 |
| JP | 2005167058 A | 6/2005 |
| JP | 2006511265 A | 4/2006 |
| JP | 2007520307 A | 7/2007 |
| JP | 2010019554 A | 1/2010 |
| JP | 2010029650 A | 2/2010 |
| JP | 2010204068 A | 9/2010 |
| JP | 2013538097 A | 10/2013 |
| JP | 2004-512502 A | 4/2014 |
| JP | 2015519970 A | 7/2015 |
| JP | 2016508808 A | 3/2016 |
| JP | 06785554 B2 | 10/2020 |
| WO | WO 94/06355 A1 | 3/1994 |
| WO | WO 02/32506 A1 | 4/2002 |
| WO | WO2005/018469 A1 | 3/2005 |
| WO | WO 2008/051484 A2 | 5/2008 |
| WO | WO2011/040054 A1 | 7/2011 |
| WO | WO 2011/092683 A1 | 8/2011 |
| WO | WO2011/154654 A2 | 12/2011 |
| WO | WO2014/008594 A1 | 1/2014 |
| WO | WO2014/071386 A1 | 5/2014 |
| WO | WO2015/000953 A1 | 1/2015 |

OTHER PUBLICATIONS

Appel et al.; Stereoscopic highspeed recording of bubble filaments; Ultrasonics Sonochemistry; vol. 11(1); pp. 39-42; Jan. 2004.
Aran et al.; Transurethral prostate magnetic resonance elestography; prospective imaging requirements; Magn. Reson. Med.; 65(2); pp. 340-349; Feb. 2011.
Aschoff et al.; How does alteration of hepatic blood flow affect liver perfusion and radiofrequency-induced thermal lesion size in rabbit liver?; J Magn Reson Imaging; 13(1); pp. 57-63; Jan. 2001.
Atchley et al.; Thresholds for cavitation produced in water by pulsed ultrasound; Ultrasonics.; vol. 26(5); pp. 280-285; Sep. 1988.
AVAGO Technologies; ACNV2601 High Insulation Voltage 10 MBd Digital Opotcoupler. Avago Technologies Data Sheet; pp. 1-11; Jul. 29, 2010.
Avago Technologies; Avago's ACNV2601 optocoupler is an optically coupled logic gate; Data Sheet; 2 pages; Jul. 29, 2010.
AVTECH; AVR-8 Data sheet; May 23, 2004; 3 pages; retrieved from the internet (http//www.avtechpulse.com).
Bjoerk et al.; Cool/MOS CP—How to make most beneficial use of the generation of super junction technology devices. Infineon Technologies AG. Feb. 2007 [retrieved Feb. 4, 2014] from the internet (http://www.infineon.com/dgdl/Infineon+-+Application+Note+-+PowerMOSFETs+-+600V+CoolMOS%E284%A2+-+CP+Most+beneficial+use+of+superjunction+technologie+devices.pdf?folderId=db3a304412b407950112b408e8c90004&fileId=db3a3044 12b407950112b40ac9a40688>pp. 1, 4, 14.
Bland et al.; Surgical Oncology; McGraw Hill; Chap. 5 (Cavitron Ultrasonic Aspirator); pp. 461-462; Jan. 29, 2001.
Burdin et al.; Implementation of the laser diffraction technique for cavitation bubble investigations; Particle & Particle Systems Characterization; vol. 19; pp. 73-83; May 2002.
Cain, Charles A.; Histotripsy: controlled mechanical sub-division of soft tissues by high intensity pulsed ultrasound (conference presentation); American Institute of Physics (AIP) Therapeutic Ultrasound: 5th International Symposium on Therapeutic Ultrasound; 44 pgs.; Oct. 27-29, 2005.
Canney et al.; Shock-Induced Heating and Millisecond Boiling in Gels and Tissue Due to High Intensity Focused Ultrasound; Ultrasound in Medicine & Biology, vol. 36, pp. 250-267; Feb. 2010 (author manuscript).
Chan et al.; An image-guided high intensity focused ultrasound device for uterine fibroids treatment; Medical Physics, vol. 29, pp. 2611-2620, Nov. 2002.
Clasen et al.; MR-guided radiofrequency ablation of hepatocellular carcinoma: Long-term effectiveness; J Vasc Interv Radiol; 22(6); pp. 762-770; Jun. 2011.
Clement et al.; A hemisphere array for non-invasive ultrasound brain therapy and surgery; Physics in Medicine and Biology, vol. 45, p. 3707-3719, Dec. 2000.
Cline et al.; Magnetic resonance-guided thermal surgery; Magnetic Resonance in Medicine; 30(1); pp. 98-106; Jul. 1993.
Curiel et al.; Elastography for the follow-up of high-intensity focused ultrasound prostate cancer treatment: Initial comparison with MRI; Ultrasound Med. Biol; 31(11); pp. 1461-1468; Nov. 2005.
Desilets et al.; The Design of Efficient Broad-Band Piezoelectric Transducers; Sonics and Ultrasonics, IEEE Transactions on, vol. 25, pp. 115-125, May 1978.
Emelianov et al.; Triplex ultrasound: Elasticity imaging to age deep venous thrombosis; Ultrasound Med Biol; 28(6); pp. 757-767; Jun. 2002.
Giannatsis et al.; Additive fabrication technologies applied to medicine and health care: a review; The International Journal of Advanced Manufacturing Technology; 40(1-2); pp. 116-127; Jan. 2009.
Gudra et al.; Influence of acoustic impedance of multilayer acoustic systems on the transfer function of ultrasonic airborne transducers; Ultrasonics, vol. 40, pp. 457-463, May 2002.
Hall et al.; A Low Cost Compact 512 Channel Therapeutic Ultrasound System for Transcutaneous Ultrasound Surgery; AIP Conference Proceedings, Boston, MA; vol. 829, pp. 445-449, Oct. 27-29, 2005.
Hall et al.; Acoustic Access to the Prostate for Extracorporeal Ultrasound Ablation; Journal of Endourology, vol. 24, pp. 1875-1881, Nov. 2010.
Hall et al.; Histotripsy of the prostate: dose effects in a chronic canine model; Urology; 74(4); pp. 932-937; Oct. 2009 (author manuscript).
Hall et al.; Imaging feedback of tissue liquefaction (histotripsy) in ultrasound surgery; IEEE Ultrasonic Symposium, Sep. 18-21, 2005, pp. 1732-1734.
Hartmann; Ultrasonic properties of poly(4-methy pentene-1), Journal of Applied Physics, vol. 51, pp. 310-314, Jan. 1980.
Holland et al.; Thresholds for transient cavitation produced by pulsed ultrasound in a controlled nuclei environment; J. Acoust. Soc. Am.; vol. 88(5); pp. 2059-2069; Nov. 1990.
Huber et al.; Influence of shock wave pressure amplitude and pulse repetition frequency on the lifespan, size and number of transient cavities in the field of an electromagnetic lithotripter; Physics in Medicine and Biology; vol. 43(10); pp. 3113-3128; Oct. 1998.
Hynynen et al.; Tissue thermometry during ultrasound exposure; European Urology; 23(Suppl 1); pp. 12-16; (year of pub. sufficiently earlier than effective US filing date and any foreign priority date)1993.
Kallel et al.; The feasibility of elastographic visualization of HIFU-induced thermal lesions in soft tissues: Image-guided high-intensity focused ultrasound; Ultrasound Med. Biol; 25(4); pp. 641-647; May 1999.

(56) References Cited

OTHER PUBLICATIONS

Kim et al.; Dependence of particle volume fraction on sound velocity and attenuation of EPDM composites; Ultrasonics, vol. 46, pp. 177-183, Feb. 2007.
Konofagou; Quo vadis elasticity imaging?; Ultrasonics; 42(1-9); pp. 331-336; Apr. 2004.
Krimholtz et al.; New equivalent circuits for elementary piezoelectric transducers; Electronics Letters, vol. 6, pp. 398-399, Jun. 1970.
Kruse et al.; Tissue characterization using magnetic resonance elastography: Preliminary results; Phys. Med. Biol; 45(6); pp. 1579-1590; Jun. 2000.
Lake et al.; Histotripsy: minimally invasive technology for prostatic tissue ablation in an in vivo canine model; Urology; 72(3); pp. 682-686; Sep. 2008.
Lauterborn et al.; Cavitation bubble dynamics studied by high speed photography and holography: part one; Ultrasonics; vol. 23; pp. 260-268; Nov. 1985.
Lensing et al.; Deep-vein thrombosis; The Lancet, vol. 353, pp. 479-485, Feb. 6, 1999.
Lin et al.; Dual-beam histotripsy: a low-frequency pump enabling a high-frequency probe for precise lesion formation; IEEE Trans. Ultrason. Ferroelectr. Control; 61(2); pp. 325-340; Feb. 2014; (Author Manuscript; 29 pages).
Liu et al.; Real-time 2-D temperature imaging using ultrasound; IEEE Trans Biomed Eng; 57(1); pp. 12-16; Jan. 2010 (author manuscript, 16 pgs.).
Liu et al.; Viscoelastic property measurement in thin tissue constructs using ultrasound; IEEE Trans Ultrason Ferroelectr Freq Control; 55(2); pp. 368-383; Feb. 2008 (author manuscript, 37 pgs.).
Manes et al.; Design of a Simplified Delay System for Ultrasound Phased Array Imaging; Sonics and Ultrasonics, IEEE Transactions on, vol. 30, pp. 350-354, Nov. 1983.
Maréchal et al; Effect of Radial Displacement of Lens on Response of Focused Ultrasonic Transducer; Japanese Journal of Applied Physics, vol. 46, p. 3077-3085; May 15, 2007.
Maréchal et al; Lens-focused transducer modeling using an extended KLM model; Ultrasonics, vol. 46, pp. 155-167, May 2007.
Martin et al.; Water-cooled, high-intensity ultrasound surgical applicators with frequency tracking; Ultrasonics, Ferroelectrics and Frequency Control, IEEE Transactions on, vol. 50, pp. 1305-1317, Oct. 2003.
Maxwell et al.; Cavitation clouds created by shock scattering from bubbles during histotripsy; J. Acoust. Soc. Am.; 130(4); pp. 1888-1898; Oct. 2011.
Maxwell et al.; Noninvasive Thrombolysis Using Pulsed Ultrasound Cavitation Therapy—Histotripsy; Ultrasound in Medicine & Biology, vol. 35, pp. 1982-1994, Dec. 2009 (author manuscript).
Maxwell; Noninvasive thrombolysis using histotripsy pulsed ultrasound cavitation therapy; PhD Dissertation. University of Michigan, Ann Arbor, Michigan. Jun. 2012.
Miller et al.; A review of in vitro bioeffects of inertial ultrasonic cavitation from a mechanistic perspective; Ultrasound in Medicine and Biology; vol. 22; pp. 1131-1154; (year of publication is sufficiently earlier than the effective U.S. filing date and any foreign priority date) 1996.
Nightingale et al.; Analysis of contrast in images generated with transient acoustic radiation force; Ultrasound Med Biol; 32(1); pp. 61-72; Jan. 2006.
Ohl et al.; Bubble dynamics, shock waves and sonoluminescence; Phil. Trans. R. Soc. Lond. A; vol. 357; pp. 269-294; (year of publication is sufficiently earlier than the effective U.S. filing date and any foreign priority date) 1999.
Okada et al.; A case of hepatocellular carcinoma treated by MR-guided focused ultrasound ablation with respiratory gating; Magn Reson Med Sci; 5(3); pp. 167-171; Oct. 2006.
Palmeri et al.; Acoustic radiation force-based elasticity imaging methods; Interface Focus; 1; pp. 553-564; Aug. 2011.
Parsons et al.; Cost-effective assembly of a basic fiber-optic hydrophone for measurement of high-amplitude therapeutic ultrasound fields; The Journal of the Acoustical Society of America, vol. 119, pp. 1432-1440, Mar. 2006.
Parsons et al.; Pulsed cavitational ultrasound therapy for controlled tissue homogenization; Ultrasound in Med. & Biol.; vol. 32(1); pp. 115-129; Jan. 2006.
Pishchalnikov et al.; Cavitation Bubble Cluster Activity in the Breakage of Kidney Stones by Lithotripter Shock Waves; J Endourol.; 17(7): 435-446; Sep. 2003.
Porter et al.; Reduction in left ventricular cavitary attenuation and improvement in posterior myocardial contrast . . . ; J Am Soc Echocardiography; pp. 437-441; Jul.-Aug. 1996.
Roberts et al.; Pulsed cavitational ultrasound: a noninvasive technology for controlled tissue ablation (histotripsy) in the rabbit kidney; Journal of Urology; vol. 175(2); pp. 734-738; Feb. 2006.
Rosenschein et al.; Ultrasound Imaging-Guided Noninvasive Ultrasound Thrombolysis: Preclinicai Results; Circulation; vol. 102; pp. 238-245, Jul. 11, 2000.
Rowland et al.; MRI study of hepatic tumours following high intensity focused ultrasound surgery; British Journal of Radiology; 70; pp. 144-153; Feb. 1997.
Roy et al.; A precise technique for the measurement of acoustic cavitation thresholds and some preliminary results; Journal of the Acoustical Society of America; vol. 78(5); pp. 1799-1805; Nov. 1985.
Sapareto et al.; Thermal dose determination in cancer therapy; Int J Radiat Oncol Biol Phys; 10(6); pp. 787-800; Apr. 1984.
Sapozhnikov et al.; Ultrasound-Guided Localized Detection of Cavitation During Lithotripsy in Pig Kidney in Vivo; IEEE Ultrasonics Symposium, vol. 2; pp. 1347-1350; Oct. 7-10, 2001.
Sato et al.; Experimental Investigation of Phased Array Using Tapered Matching Layers. 2002 IEEE Ultrasound Symposium. vol. 2; pp. 1235-1238, Oct. 2002.
Simonin et al.; Characterization of heterogeneous structure in a polymer object manufactured by stereolithography with low-frequency microechography; Journal of Materials Chemistry; vol. 6, pp. 1595-1599, Sep. 1996.
Sokolov et al.; Use of a dual-pulse lithotripter to generate a localized and intensified cavitation field; Journal of the Acoustical Society of America; vol. 110(3); pp. 1685-1695; Sep. 2001.
Song et al.; Feasibility of Using Lateral Mode Coupling Method for a Large Scale Ultrasound Phased Array for Noninvasive Transcranial Therapy; Biomedical Engineering; IEEE Transactions on, vol. 57, pp. 124-133; Jan. 2010 (author manuscript).
Souchon et al.; Visualisation of HIFU lesions using elastography of the human prostate in vivo: Preliminary results; Ultrasound Med. Biol; 29(7); pp. 1007-1015; Jul. 2003.
Souquet et al.; Design of Low-Loss Wide-Band Ultrasonic Transducers for Noninvasive Medical Application; Sonics and Ultrasonics, IEEE Transactions on, vol. 26, pp. 75-80, Mar. 1979.
Therapeutic Ultrasound Group. Non-invasive Ultrasonic Tissue Fraction for Treatment of Benign Disease and Cancer—"Histotripsy". University research [online]. Biomedical Engineering Department, University of Michigan. Jul. 2011[retrieved on Jan. 28, 2014] from: (http://web.archive.org/web/20110720091822/http://www.histotripsy.umich.edu/index.html>.entiredocument).
Toda; Narrowband impedance matching layer for high efficiency thickness mode ultrasonic transducers; Ultrasonics, Ferroelectrics and Frequency Control, IEEE Transactions on, vol. 49, pp. 299-306, Mar. 2002.
Van Kervel et al.; A calculation scheme for the optimum design of ultrasonic transducers; Ultrasonics, vol. 21, pp. 134-140, May 1983.
Wang et al.; Quantitative ultrasound backscatter for pulsed cavitational ultrasound therapy-histotripsy; Ultrasonics, Ferroelectrics and Frequency Control, IEEE Transactions on, vol. 56, pp. 995-1005, May 2009.
Xie et al.; Correspondence of ultrasound elasticity imaging to direct mechanical measurement in aging DVT in rats; Ultrasound Med Biol; 31(10); pp. 1351-1359; Oct. 2005 (author manuscript, 20 pgs.).

(56) References Cited

OTHER PUBLICATIONS

Xu et al.; A new strategy to enhance cavitational tissue erosion by using a high intensity initiating sequence; IEEE Trans Ultrasonics Ferroelectrics and Freq Control; vol. 53(8); pp. 1412-1424; Aug. 2006.

Xu et al.; Controlled ultrasound tissue erosion: the role of dynamic interaction between insonation and microbubble activity; Journal of the Acoustical Society of America; vol. 117(1); pp. 424-435; Jan. 2005.

Xu et al.; Controlled ultrasound tissue erosion; IEEE Transaction on Ultrasonics, Ferroelectrics, and Frequency Control; vol. 51 (6); pp. 726-736; Jun. 2004.

Xu et al.; Effects of acoustic parameters on bubble cloud dynamics in ultrasound tissue erosion (histotripsy); Journal of the Acoustical Society of America; vol. 122(1); pp. 229-236; Jul. 2007.

Xu et al.; High Speed Imaging of Bubble Clouds Generated in Pulsed Ultrasound Cavitational Therapy Histotripsy; IEEE Trans Ultrason Ferroelectr Freq Control; ; vol. 54; No. 10; p. 2091R2101; Oct. 2007.

Xu et al.; Investigation of intensity threshold for ultrasound tissue erosion; Ultrasound in Med. & Biol.; vol. 31(12); pp. 1673-1682; Dec. 2005.

Xu et al.; Optical and acoustic monitoring of bubble cloud dynamics at a tissue-fluid interface in ultrasound tissue erosion; Journal of the Acoustical Society of America; vol. 121(4); pp. 2421-2430; Apr. 2007.

Yan et al.; A review of rapid prototyping technologies and systems; Computer-Aided Design, vol. 28, pp. 307-318, Apr. 1996.

Zhang et al.; A fast tissue stiffness-dependent elastography for HIFU-induced lesions inspection; Ultrasonics; 51(8); pp. 857-869; Dec. 2011.

Zheng et al.; An acoustic backscatter-based method for localization of lesions induced by high-intensity focused ultrasound; Ultrasound Med Biol; 36(4); pp. 610-622; Apr. 2010.

Billson et al.; Rapid prototyping technologies for ultrasonic beam focussing in NDE; IEEE International Ultrasonic Symposium Proceedings; pp. 2472-2472; Oct. 2011.

Wikipedia; Medical ultrasound; 15 pages; retrieved from the internet (https://en.wikipedia.org/w/index.php?title=Medical_utrasound &oldid=515340960) on Jan. 12, 2018.

Xu et al.; U.S. Appl. No. 15/713,441 entitled "Bubble-induced color doppler feedback during histotripsy," filed Sep. 22, 2017.

Hall et al.; U.S. Appl. No. 15/583,852 entitled "Method of manufacturing an ultrasound system," filed May 1, 2017.

Hobarth et al.; Color flow doppler sonography for extracorporal shock wave lithotripsy; Journal of Urology; 150(6); pp. 1768-1770; Dec. 1, 1993.

Maxwell et al.; In-vivo study of non-invasive thrombolysis by histotripsy in a porcine model; IEEE international Ultrasonics Symposium; IEEE; p. 220-223; Sep. 20, 2009.

Urban et al.; Measurement of prostate viscoelasticity using shearwave dispersion ultrasound vibrometry (SDUV): an in vitro study; IEEE International Ultrasonics Symposium Proceedings (IUS); pp. 1141-1144; Oct. 11, 2010.

Khokhlova et al.; Controlled tissue emulsification produced by high intensity focused ultrasound shock waves and millisecond boiling; J. Acoust. Soc. Am.; 130(5), pt. 2; pp. 3498-3510; Nov. 2011.

Miller et al.; Investigation of the mechanism of ARFI-based color doppler feedback of histotripsy tissue fractionation; Ultrasonic Symposium (IUS); 2013 IEEE International; 4 pages; Jul. 21-25, 2013.

Miller et al.; Real-time elastography-based monitoring of histotripsy tissue fractionation using color doppler; Ultrasonics Symposium (IUS); 2012 IEEE International; 8 pages; Oct. 7-10, 2012.

Cain et al.; U.S. Appl. No. 14/911,273 entitled "Histotripsy using very short ultrasound pulses," filed Feb. 10, 2016.

Bak; Rapid prototyping or rapid production? 3D printing processes move industry towards the latter; Assembly Automation; 23(4); pp. 340-345; Dec. 1, 2003.

Shung; Diagnostic Ultrasound: Imaging and Blood Flow Measurements; Taylor and Francis Group, LLC; Boca Raton, FL; 207 pages; (year of pub. sufficiently earlier than effective US filing date and any foreign priority date) 2006.

Cannata et al.; U.S. Appl. No. 16/930,181 entitled "Histotripsy systems and methods," filed Jul. 15, 2020.

Maxwell et al.; The role of compressional pressure in the formation of dense bubble clouds in histotripsy; 2009 IEEE International Ultrasonics Symposium; pp. 81-84; Sep. 20, 2009.

\* cited by examiner

Fig. 4A
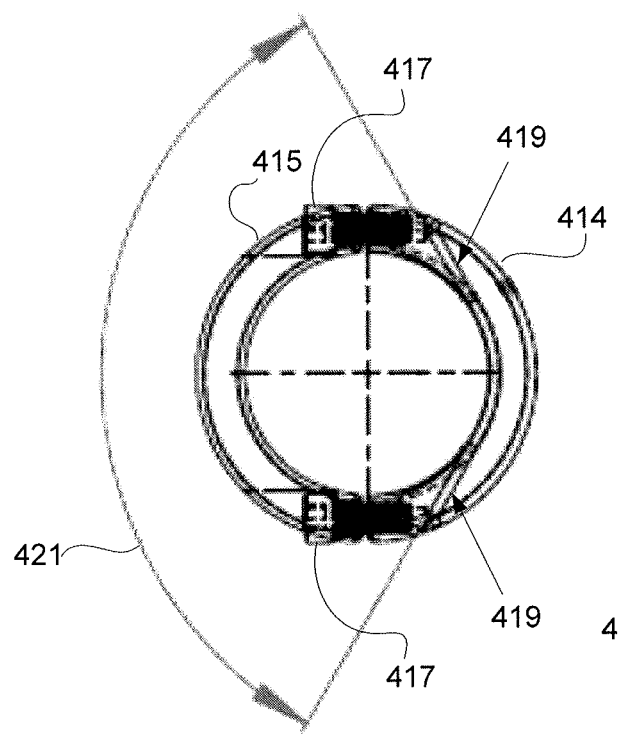
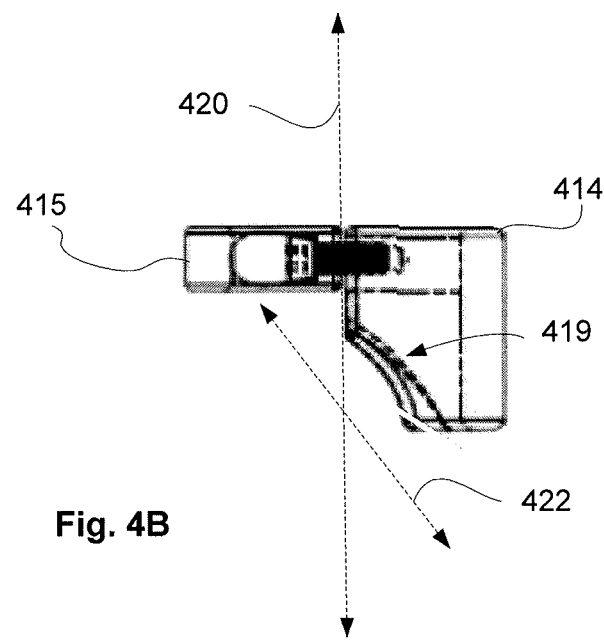
Fig. 4B

ARTICULATING ARM LIMITER FOR CAVITATIONAL ULTRASOUND THERAPY SYSTEM

CROSS REFERENCE TO RELATED APPLICATIONS

This application claims the benefit under 35 U.S.C. 119 of U.S. Provisional Patent Application No. 61/842,811, filed Jul. 3, 2013, titled "Articulating Arm Limiter for Cavitational Ultrasound Therapy System", which application is incorporated herein by reference.

INCORPORATION BY REFERENCE

All publications and patent applications mentioned in this specification are herein incorporated by reference to the same extent as if each individual publication or patent application was specifically and individually indicated to be incorporated by reference.

FIELD

This disclosure relates generally to support and positioning apparatuses for ultrasound therapy systems. More specifically, this disclosure relates to micromanipulator systems with improved control and safety over prior systems.

BACKGROUND

Histotripsy and Lithotripsy are non-invasive tissue ablation modalities that focus pulsed ultrasound from outside the body to a target tissue inside the body. Histotripsy mechanically damages tissue through cavitation of micro bubbles which homogenizes cellular tissues into an a-cellular liquid that can be expelled or absorbed by the body, and Lithotripsy is typically used to fragment urinary stones with acoustic shockwaves.

Histotripsy is the mechanical disruption via acoustic cavitation of a target tissue volume or tissue embedded inclusion as part of a surgical or other therapeutic procedure. Histotripsy works best when a whole set of acoustic and transducer scan parameters controlling the spatial extent of periodic cavitation events are within a rather narrow range. Small changes in any of the parameters can result in discontinuation of the ongoing process.

Histotripsy requires high peak intensity acoustic pulses which in turn require large surface area focused transducers. These transducers are often very similar to the transducers used for Lithotripsy and often operate in the same frequency range. The primary difference is in how the devices are driven electrically.

Histotripsy pulses consist of a (usually) small number of cycles of a sinusoidal driving voltage whereas Lithotripsy is (most usually) driven by a single high voltage pulse with the transducer responding at its natural frequencies. Even though the Lithotripsy pulse is only one cycle, its negative pressure phase length is equal to or greater than the entire length of the Histotripsy pulse, lasting tens of microseconds. This negative pressure phase allows generation and continual growth of the bubbles, resulting in bubbles of sizes up to 1 mm. The Lithotripsy pulses use the mechanical stress produced by a shockwave and these 1 mm bubbles to cause tissue damage or fractionate stones.

In comparison, each negative and positive cycle of a Histotripsy pulse grows and collapses the bubbles, and the next cycle repeats the same process. The maximal sizes of bubbles reach approximately tens to hundreds of microns. These micron size bubbles interact with a tissue surface to mechanically damage tissue.

In addition, Histotripsy delivers hundreds to thousands of pulses per second, i.e., 100-1 kHz pulse repetition frequency. Lithotripsy only works well within a narrow range of pulse repetition frequency (usually 0.5-1 Hz). Studies show that the efficacy and efficiency of lithotripsy decreases significantly when the pulse repetition frequency is increased to 10-100 Hz. The reduced efficiency is likely due to the increased number of mm size bubbles blocking the shock waves and other energy from reaching the stone.

Histotripsy typically comprises delivering acoustic pulses that operate at a frequency between approximately 50 KHz and 5 MHz, having a pulse intensity with a peak negative pressure of approximately 8-40 MPa, a peak positive pressure of more than 10 MPa, a pulse length shorter than 50 cycles, a duty cycle between approximately 0.1% and 5% and in some embodiments less than 5%, and a pulse repetition frequency of less than 5 KHz.

Diagnostic ultrasound can be used during Histotripsy procedures to visualize the surgical anatomy and monitor the process in real time. The Histotripsy cavitation bubble cloud can appear very clearly on diagnostic ultrasound as a hyperechoic (light) region and ablated homogenized tissue can appear as a hypoechoic (dark) region. Large and irregular tissue volumes can be ablated using Histotripsy by electronically changing the focus of a therapeutic array or by mechanically moving the focus of the therapeutic transducer within the surgical target area.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIGS. 4A-4B show different views of an arm limiter for an articulating arm.

SUMMARY OF THE DISCLOSURE

An articulating arm is provided, comprising a first articulating arm link, a second articulating arm link, a rotating joint configured to rotationally connect the first articulating arm link to the second articulating arm link so that the first and second articulating arm links are substantially perpendicular, and an arm limiter attached to the second articulating arm link, the arm limiter being configured to limit rotation of the second articulating arm link along the rotating joint with respect to the first articulating arm link.

In some embodiments, the arm limiter further comprising a collar portion and a stop limiting portion, the collar portion and the stop limiting portion being configured to attach together around the second articulating arm link.

In one embodiment, the stop limiting portion includes cutouts configured to engage with and conform to the first articulating link when a specified maximum rotation of the second articulating arm has been reached.

In one embodiment, the arm further comprises a weight compensator attached to the first articulating arm link and configured to reduce a load on the articulating arm.

In some embodiments, the arm limiter is set to an appropriate angle in order to prevent undesirable recoiling of the weight compensator and therefore jerk motion on the end of the articulating arm.

An ultrasound therapy system is provided, comprising an articulating arm having a first articulating arm link, a second articulating arm link, a rotating joint configured to rotationally connect the first articulating arm link to the second articulating arm link so that the first and second articulating arm links are substantially perpendicular, and an arm limiter attached to the second articulating arm link, the arm limiter being configured to limit rotation of the second articulating arm link along the rotating joint with respect to the first articulating arm link, an ultrasound therapy transducer mounted the articulating arm; and an imaging system mounted to the articulating arm.

In one embodiment, the system further comprises a handle portion coupled to the articulating arm, wherein manipulation of the handle portion adjusts the articulating arm from a locked configuration in which the articulating arm cannot be moved to an unlocked configuration in which the articulating arm can be moved and positioned.

DETAILED DESCRIPTION

Figure 1:
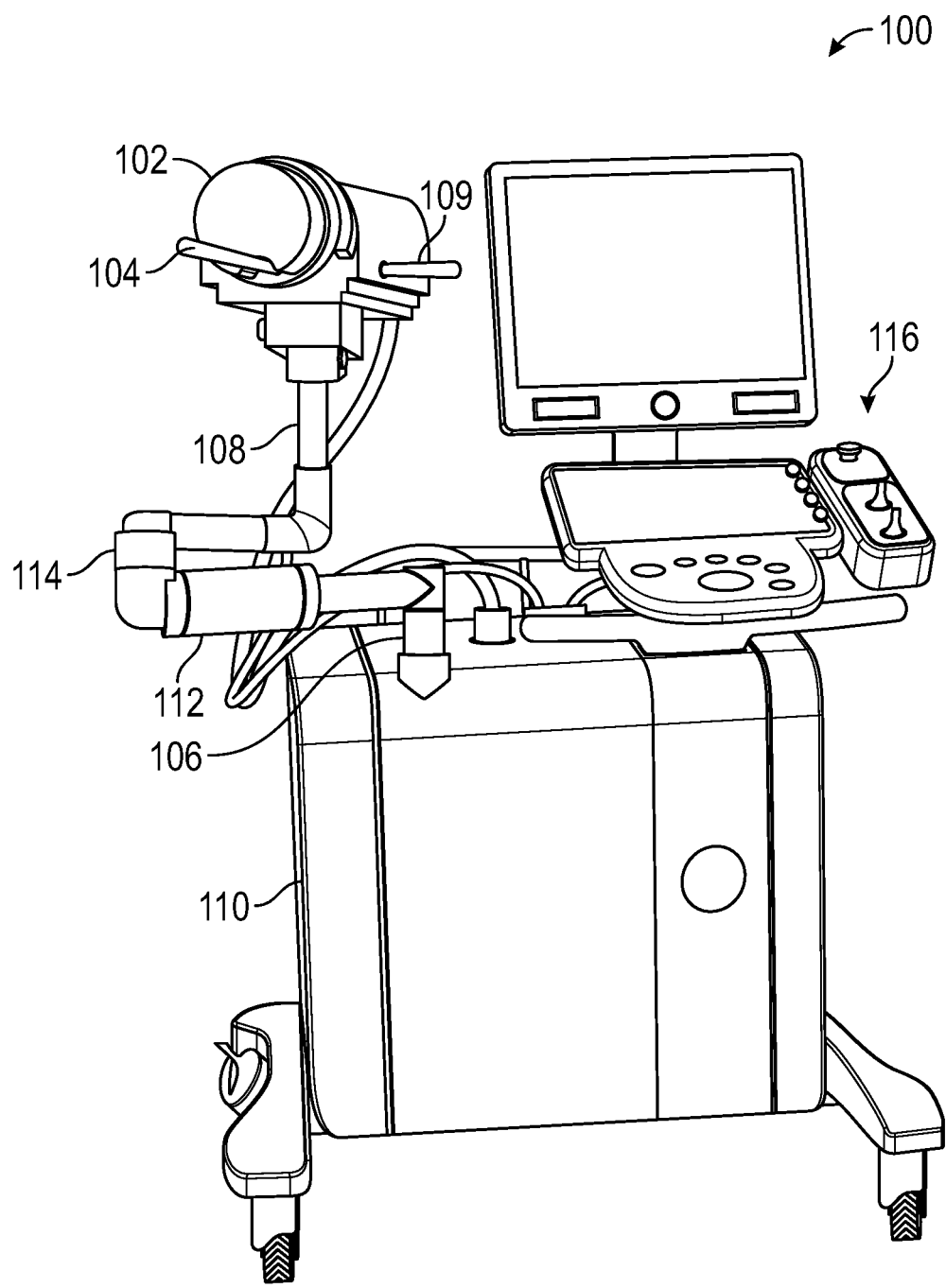
FIG. 1 illustrates one embodiment of an ultrasound therapy system including an articulating arm with an arm limiter.

FIG. 1 shows a micromanipulator system 100 configured to support and control the movement of an ultrasound therapy transducer 102 and/or an imaging system 104, such as a transrectal imaging probe. The system can include an articulating arm 106 that can include a plurality of links and joints to move with up to 6 degrees of freedom, and a handle 108 (e.g., a pistol grip) that can be manipulated by a user to control movement of the system. The handle 108 can be actuated by the user to lock the articulating arm in place, or unlock the articulating arm to allow for movement and positioning of the system. Additionally, a side handle 109 can be attached to the micromanipulator to help the user hold and position the micromanipulator system with one hand while the other hand holds the handle 108 on the articulating arm. The therapy transducer 102, imaging system 104, and articulating arm 106 can all be supported by and attached to a portable cart 110, which can include the power generator(s) and/or electronic controller(s) 116, and any additional hardware and software needed to control and operate the therapy and imaging systems, as well as input devices (e.g., keyboard, GUI) and display devices for treatment planning, execution, and monitoring.

In some embodiments, the micromanipulator system is configured for treatment of benign prostatic hyperplasia. For example, the therapy transducer 102 can be configured to direct focused ultrasound energy from the perineum to the prostate of a patient, while the imaging system 104 provides ultrasound images of the prostate and therapy. In one embodiment of the system 100, the articulating arm 106 can be configured to hold and precisely position the components and cabling described above, which can weigh upwards of 15 lbs.

Still referring to FIG. 1, a weight compensator 112 can be attached to at least one of a plurality of articulating joints in the articulating arm 106 to reduce a vertical load on the articulating arm. In one embodiment, the weight compensator 112 can be a spring loaded mechanism that works against gravity so that the user does not need to carry all the weight of the system. The compensator can be applied to a joint or link that handles vertical motion in order to reduce the overall weight of the system carried by the user. In some instances, the weight compensator can recoil, causing a sudden jerk or movement in the articulating arm. These sudden jerks or movements can cause injury to the patient if the imaging probe is positioned within the patient. To prevent sudden jerks in the articulating arm 106, at least one arm motion limiter 114 can be installed on the arm to reduce rotation at one or more joints of the arm to a specified rotation amount, which can thereby prevent recoil of the weight compensator. This arm motion limiter will be described in more detail below.

Figure 2A:
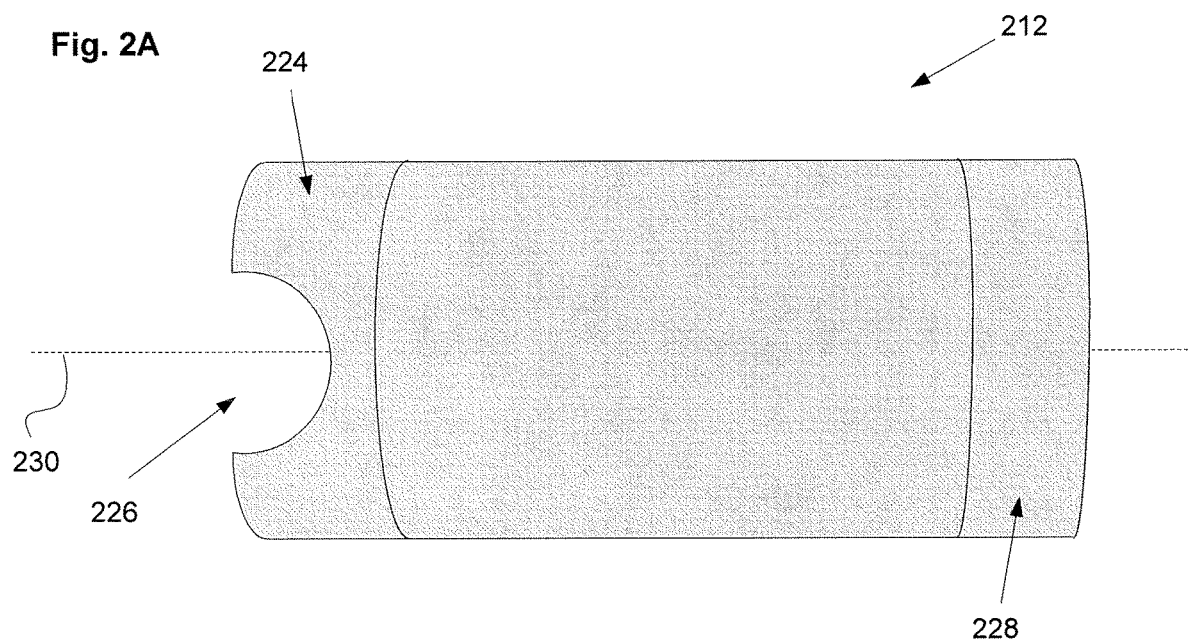
FIGS. 2A-2B illustrates the weight compensator and articulating arm of the system of FIG. 1.

FIG. 2A shows a schematic view of a weight compensator 212. The weight compensator can include a spring-loaded compensating end 224 having a cutout 226 configured to engage an adjacent link or joint of an articulating arm. The weight compensator 212 can mount on a first link (such as a horizontal link represented by line 230) and the cutout 226 can engage with an adjacent second link that is substantially perpendicular to the first link. The spring-loaded compensating end 224 can then compensate for the weight of the articulating arm by reducing a vertical load on the arm. The tension of the weight compensator can be adjusted by twisting or rotating adjusting ring 228.

Figure 2B:
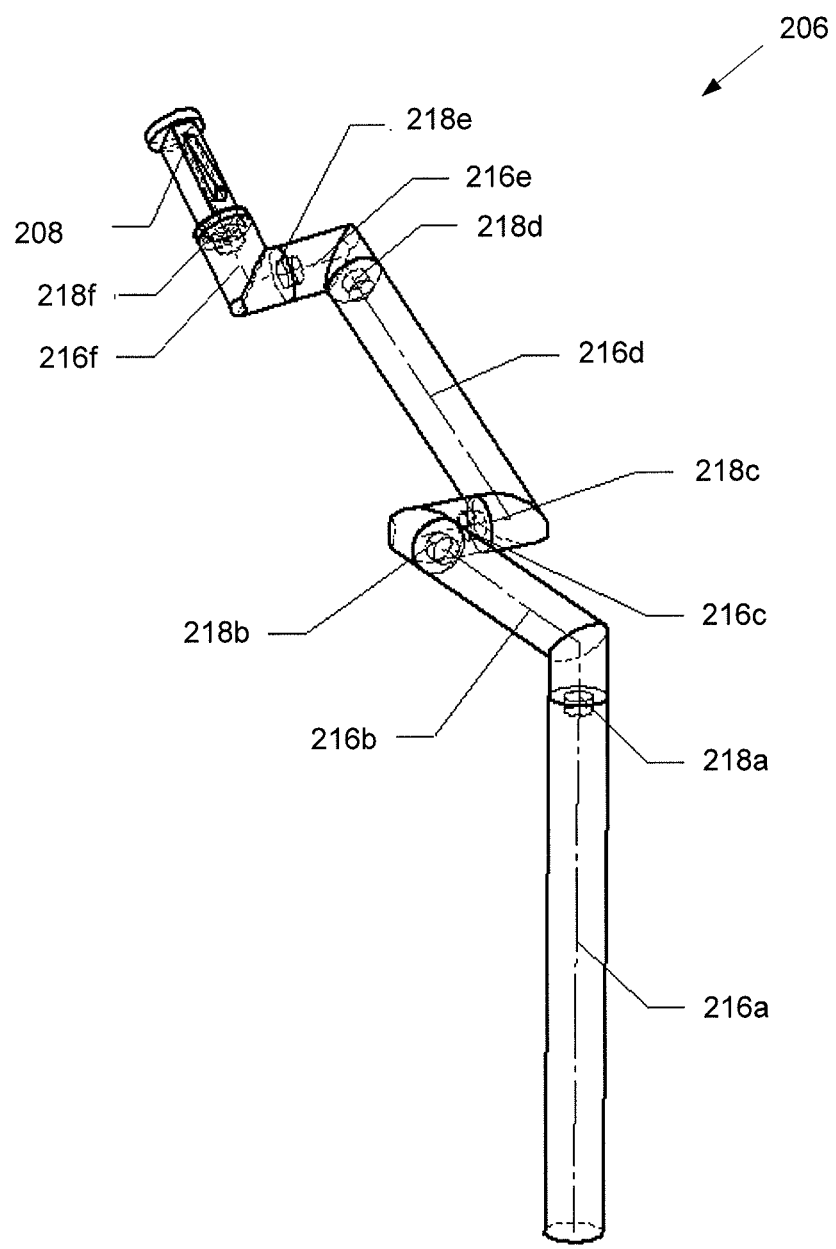

Referring now to FIG. 2B, an articulating arm 206 can include multiple links 216a-216f interconnected by rotational joints 218a-218f, respectively. In one embodiment, the links can comprise aluminum rods having an outer diameter of 25-100 mm. Each joint connects two neighboring links and enables up to 360 degrees of relative motion between the neighboring links. As a system, these links and joints offer a wide range of motion with up to 6 degrees of freedom for the articulating arm 206. One end of the articulating arm (e.g., the distal end) can comprise the handle 208 described above.

When the handle 208 is disengaged (at rest) the links of the articulating arm can be locked in place so as to fix the position of the articulating arm. Engaging (squeezing) the handle 208 can unlock the rotational joints and enable the surgeon or user to position the therapy transducer and imaging system. When the handle is engaged, the surgeon or user must support the weight of both the therapy transducer and imaging system, and the weight of half of the arm (e.g., a combined weight of approximately 15 lbs). It can be challenging to deftly manipulate this load in all directions and can lead to safety issues, such as the potential to injure the patient's rectum with the imaging probe as it is being positioned in the rectum for prostate imaging.

As described above, a spring-loaded weight compensator can be added to compensate the arm load on one or more joints. When mounted on a horizontal link, as shown in FIG. 1, the spring can compensate for the vertical load or weight in the up/down direction. This configuration can eliminate the sudden weight load that occurs when the pistol grip handle is released, and eases or eliminates the weight burden of the system as the surgeon inserts the imaging probe into the rectum. However, one significant drawback with the weight compensator is that can recoil when the arm link is fully extended, which can cause a sudden jerk in the arm. This sudden jerk is a safety issue since the sudden recoil could harm the patient.

An arm limiter can be mounted to the articulating arm to eliminate the potential for the weight compensator to recoil.

This can be done by limiting the rotation of specific links around its adjacent link. Still referring to FIG. 2B, in one specific embodiment, the rotation of link 216d can be limited to a specific range of motion (e.g., limited to 120 degrees of rotation) around link 216c with an arm limiter installed at joint 218c (between links 216c and 216d). Additionally, this arm limiter can restrict the rotation between link 216b and link 216d (when in the horizontal position) to a specific range of motion (e.g., be less than 180 degrees). In one specific embodiment, in order to eliminate the potential for recoil from the weight compensator, the arm limiter can be configured to restrict an angle between adjacent links to 150° or less. In other embodiments, the relative maximum angle between the links depends on the design of the arm.

Figure 3:
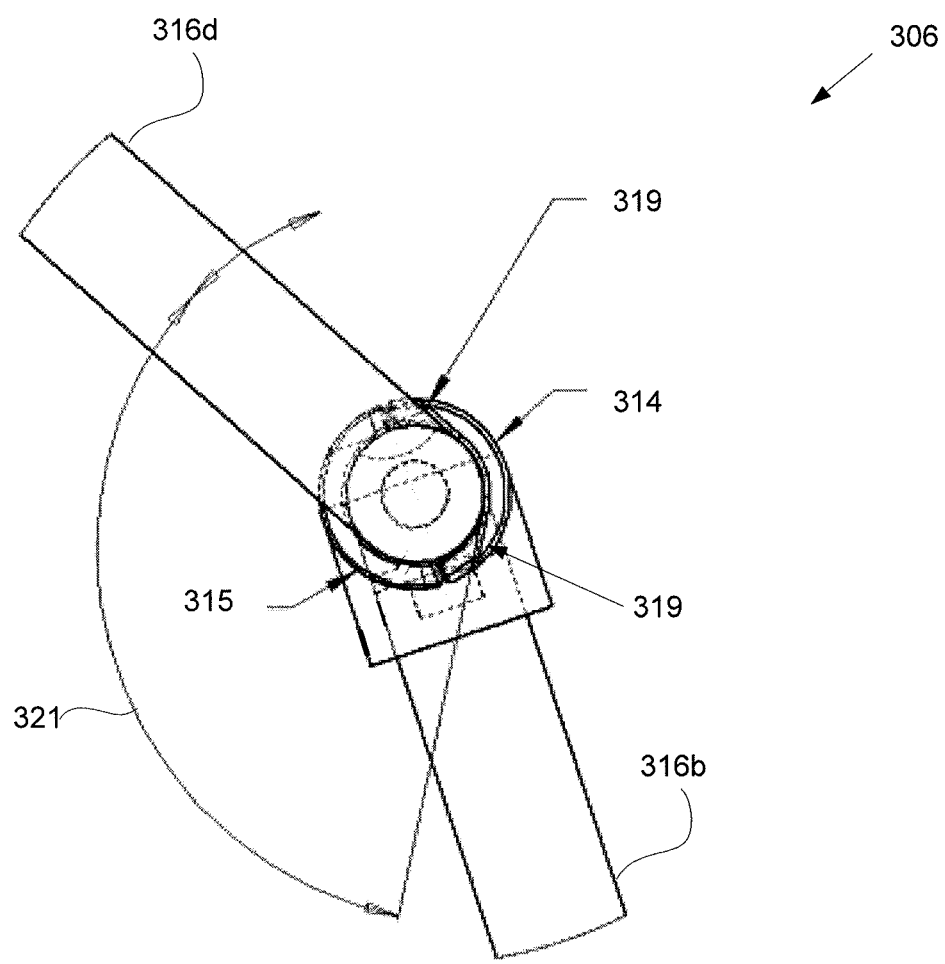
FIG. 3 illustrates a joint connecting two links of an articulating arm according to one embodiment.

FIG. 3 shows a top down view of an arm limiter 314 and arm limiter collar 315 installed between links 316b and 316d of an articulating arm 306. Note that links 316b and 316d are in the same plane (the plane of the page) and that there may be another central link not shown in the drawing perpendicular to links 316b and 316 that extends out of the plane of the page (similar to the arrangement of links 216b, 216c, and 216d in FIG. 2B). The arm limiter can be installed on the joint between link 316d and the central link, or on the central link itself. The collar 315 holds the arm limiter 314 onto the desired link, and the arm limiter 314 includes one or more stop limit portions 319 comprising cutouts or protrusions that engage the link to be rotation limited when a desired maximum rotation has been reached. In FIG. 3, the stop limiting portion 319 limits the rotation of link 316d to a limited rotation angle 321, illustrated in FIG. 3 Therefore, the stop limiting portion 319 of the arm limiter 314 can act as physical stops that engage the desired link to physically prevents further rotation of that link. The arm limiter can be configured to limit rotation between the two links to any desired range, such as to less than 150 degrees. Furthermore, the allowed angle of rotation between the adjusted links can be adjusted which will be described in more detail below.

FIGS. 4A-4B illustrate various views of the arm limiter 414 and collar 415. FIG. 4A is a top down view, showing attachment of the arm limiter to the collar with screws 417. The collar and limiter can be clamped around the desired link or joint of the articulating arm to prevent or limit rotation of the adjacent link. As described above, stop limiting portion 419 can limit rotation of the desired link to limited rotation angle 421.

FIG. 4B shows a side view of the collar 415 and arm limiter 414. In this example, the collar and arm limiter can be clamped around a vertical link extending in direction 420 (shown as a dashed line), and stop limiting portion 419 of the arm limiter can be configured to engage and act as a stopping mechanism against the adjacent (in this example, horizontal) link extending in direction 422 (shown as a dashed line). Thus, the arm limiter can be mounted onto a joint or link extending in direction 420 to limit the rotation of a link extending in direction 422. If the links are cylindrical, for example, the stop limiting portion 419 can include cutouts or protrusions having a curvature designed to conform to the adjacent link when the maximum rotation is reached.

Figure 5:
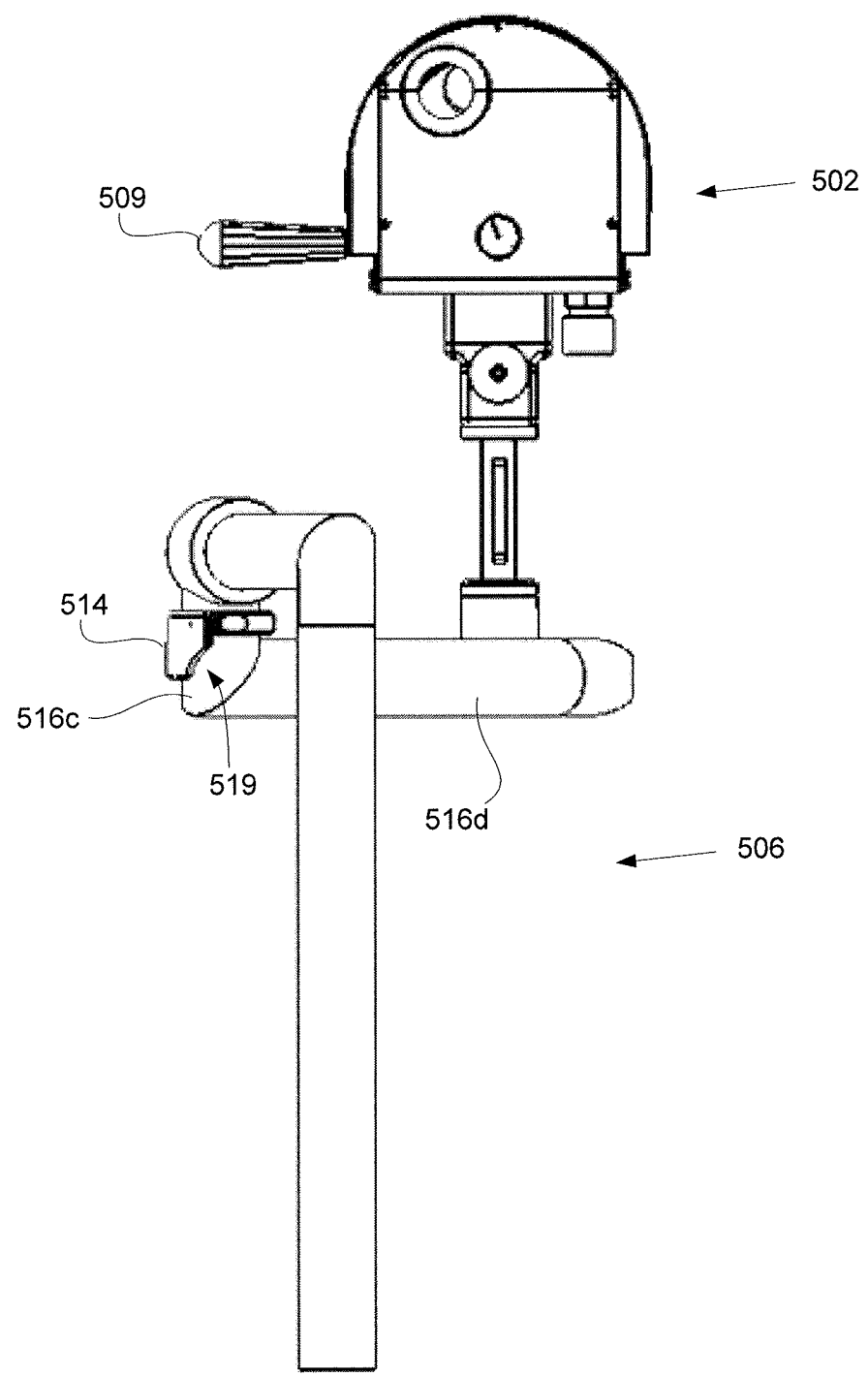
FIG. 5 shows another view of the system of FIG. 1.

FIG. 5 illustrates another view of arm limiter 514 installed on a vertical link 516c of an articulating arm 506, but not yet engaging the adjacent horizontal link 516d. The collar and cutouts or stop limiting portion 519 can also be seen in FIG. 5. FIG. 5 also shows another view of side handle 509 on the therapy transducer 502 configured to provide additional assistance for moving the load of the articulating arm by enabling the user to use two hands to support and guide the load.

Variations of the arm limiter design can restrict the manipulation of the arm and its load in different ways. Different limitation angles and/or a combination of multiple arm limiters for multiple joints could be used to meet a myriad of different load requirements and/or application requirements.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. An articulating arm, comprising:
   a first articulating arm link;
   a second articulating arm link;
   a rotating joint configured to rotationally connect the first articulating arm link to the second articulating arm link so that the first and second articulating arm links are perpendicular;
   an arm limiter attached to the second articulating arm link, the arm limiter being configured to limit rotation of the second articulating arm link along the rotating joint with respect to the first articulating arm link; and
   a weight compensator attached to the first articulating arm link and configured to reduce a load on the articulating arm, wherein the arm limiter is set to an appropriate angle in order to prevent undesirable recoiling of the weight compensator and therefore jerk motion on the end of the articulating arm.

2. The articulating arm of claim 1, the arm limiter further comprising a collar portion and a stop limiting portion, the collar portion and the stop limiting portion being configured to attach together around the second articulating arm link.

3. The articulating arm of claim 2, wherein the stop limiting portion includes cutouts configured to engage with and conform to the first articulating link when a specified maximum rotation of the second articulating arm has been reached.

4. An ultrasound therapy system, comprising:
   an articulating arm having a first articulating arm link, a second articulating arm link, a rotating joint configured to rotationally connect the first articulating arm link to the second articulating arm link so that the first and second articulating arm links are perpendicular, and an arm limiter attached to the second articulating arm link, the arm limiter being configured to limit rotation of the second articulating arm link along the rotating joint with respect to the first articulating arm link;
   a weight compensator attached to the first articulating arm link and configured to reduce a load on the articulating arm, wherein the arm limiter is set to an appropriate angle in order to prevent undesirable recoiling of the weight compensator and therefore jerk motion on the end of the articulating arm;

an ultrasound therapy transducer mounted to the articulating arm; and an imaging system mounted to the articulating arm.

5. The system of claim 4, further comprising a handle portion coupled to the articulating arm, wherein manipulation of the handle portion adjusts the articulating arm from a locked configuration in which the articulating arm cannot be moved to an unlocked configuration in which the articulating arm can be moved and positioned.

* * * * *